United States Patent [19]
Kloth

[11] Patent Number: 5,928,860
[45] Date of Patent: Jul. 27, 1999

[54] PROCESS FOR DETERMINING THE TOLERANCE, OR TOXICITY OF GASEOUS, LIQUID AND/OR VISCOUS SUBSTANCES FOR THE HUMAN OR ANIMAL ORGANISM

[76] Inventor: Sabine Kloth, Freisinger Str. 21, D-85417 Marzling, Germany

[21] Appl. No.: 09/028,467

[22] Filed: Feb. 24, 1998

[30] Foreign Application Priority Data

Feb. 25, 1997 [DE] Germany .......................... 197 07 539
Mar. 6, 1997 [DE] Germany .......................... 197 09 019

[51] Int. Cl.$^6$ ........................... C12Q 1/00; G01N 35/53; G01N 33/567
[52] U.S. Cl. ................ 435/4; 435/1.2; 435/7.1; 435/7.2; 435/7.21; 435/40.52
[58] Field of Search ............... 435/1.2, 4, 7.1, 435/7.2, 7.21, 40.52

[56] References Cited

U.S. PATENT DOCUMENTS 5,525,475  6/1996  Ladouceur .

FOREIGN PATENT DOCUMENTS 0 727 480   8/1996   European Pat. Off. .
40 20 013   3/1992   Germany .
36 35 013   5/1992   Germany .
42 29 013   3/1994   Germany .

*Primary Examiner*—Sandra E. Saucier
*Attorney, Agent, or Firm*—Hoffman, Wasson & Gitler

[57] ABSTRACT

The invention relates to a novel process for determining the tolerance, especially the toxicity of gaseous, liquid and/or viscous substances for the human or animal organism. A tissue sample, obtained without proteolytic disintegration, is placed in a chamber which has at least two compartments which are separated from each other by the tissue sample. A nutrient solution is supplied to both sides of the tissue and the tissue is exposed to a test substance on at least one side. The tissue is evaluated to determine the toxicity of the substance.

10 Claims, 1 Drawing Sheet

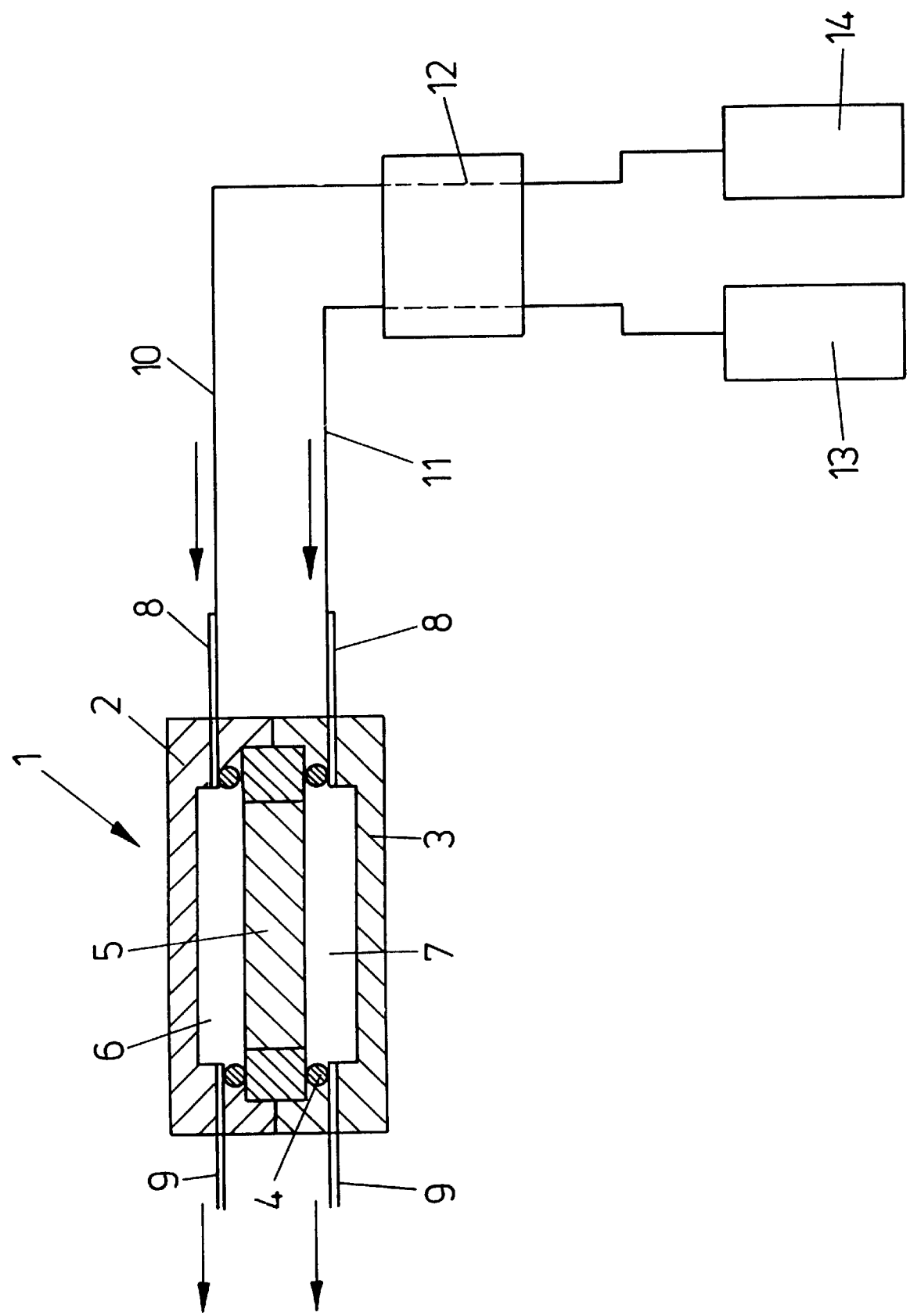

PROCESS FOR DETERMINING THE TOLERANCE, OR TOXICITY OF GASEOUS, LIQUID AND/OR VISCOUS SUBSTANCES FOR THE HUMAN OR ANIMAL ORGANISM

BACKGROUND OF THE INVENTION

In the medical and pharmaceutical fields, as well as in other areas, such as nutrition, etc., it is often necessary to determine the toxicity of certain gaseous, liquid and/or viscous substances.

The conventional processes at the present time call first of all, for cell culture tests. Subsequently animal tests are added. This is especially the case when in the cell culture tests, no toxicity has been ascertained. Then, if necessary, clinical studies on humans are undertaken. In particular, the prior art can be described as follows:

Model systems currently used to determine acute toxicity of liquid or particular substances are based on the use of cell cultures. Adherently growing cells and non-adherently growing cells are exposed for different time intervals to the substance to be tested, which is either offered with the nutrient solution or is to be colonized as a culture substrate by the cells.

Application of gaseous or liquid test substances is done in this system jointly with the test substance. Specific polar application of the test substance to the basal or apical aspect of epithelial cell monolayer is not done. The cells are either completely flushed by the medium and test substance, or exposed to both components jointly in the area of the apical cell membrane.

It is characteristic of these systems that they work only with a certain cell type. Often they are cells capable of unlimited division, such as cells with tumor characteristics.

Both epithelial cell lines and also cell lines with connective tissue characteristics are used for these tests. They differ in their properties however significantly from differentiated epithelial or connective tissue cells in human or animal organs, since tumor cells are dedifferentiated and can execute the typical cellular functions of differentiated cells only to a limited degree. According to the knowledge underlying the invention, this is one of the reasons for the lack of applicability of results obtained in cell culture experiments to the situation in the organism. Chronic toxic effects on cells are unsatisfactorily studied using cell culture systems.

If test substances in the cell culture systems have been found to be nontoxic, they must be studied for their action in an animal organism in different ways. Still, results of animal tests can only be applied to humans to a limited degree. There are major differences in the metabolic event between the human and animal organism. On the one hand, substances toxic to certain species are tolerated by humans without extensive adverse side effects (example: aspirin). On the other hand, there are a large number of test substances which are recognized as toxic to humans only in clinical studies.

One disadvantage of animal tests is that they are time-consuming and often indicate little with reference to the human organism. Likewise, clinical tests on humans are expensive and complex and often cannot be done.

In particular, a process is disclosed for the in-vitro testing of effects on biological structures in German patent No. DE 42 29 013 A1. The process is an analytic technique, and a tolerance, toxicity, side effect and efficacy test. In this process, the respective sample is placed in a chamber in which it is completely flushed by the test substance so that disadvantages arise. These are the same disadvantages that were indicated above in the discussion of cell culture tests.

Further, a system or process is known for measuring transepithelial resistances on tissue samples with a small diameter as disclosed in German Patent No. DE 40 20 013 A1. The patent uses a perfusion chamber for holding the respective tissue sample. In this system, small organisms or organs are studied with respect to their transport properties (transport systems of the membrane for ions) with special application areas of ecotoxicology, pharmacology and transport physiology in biology and medicine. The use of this known process is limited exclusively to epithelial cells. Transepithelial resistance is determined.

Further, a device is known for treatment of tissue samples held in vitro and drawn up on glass slides as described in German Patent No. DE 36 35 013 C2. The device has a chamber for holding the preparation. This chamber can be filled with the respective treatment reagent, can be sealed tight with a cover and can be provided with feed and drain openings for the reagents. It is basically a single-chamber system. The respective sample itself is located on the impermeable glass slide and is wetted on only one side by the respective test liquid. In this system, cells of the sample can only execute typical cellular functions of differentiated cells to a very limited degree, or not at all. The results obtained are not applicable or only conditionally applicable or only conditionally applicable to the actual situation in a specific organism.

Further, a device is known for determining and measuring membrane-permeable substances (see U.S. Pat. No. 5,525, 475). This device does not determine tolerance, for example, the toxicity of gaseous, liquid or viscous substances for the human or animal mechanism.

The device calls for two chambers which are separated from one another by a semipermeable membrane. The substance to be tested is placed in one of the chambers. The diffusion of the substance is measured in a second chamber. Cultivation of cells or tissues is not provided in either of these chambers. The purpose of this system is the determination of the diffusibility of a test substance, not the determination of its biological action, especially not the determination of tolerance for human or animal organisms.

An object of the invention is to devise a process which avoids these defects and enables the determination of the tolerance or toxicity of gaseous, liquid or viscous substances in the laboratory for a human or animal mechanism.

SUMMARY OF THE INVENTION

The process embodying the present invention calls for organs or organ parts which have been obtained without proteolytic disintegration from a human or animal body to be cultivated in a gradient perfusion chamber in the presence of a substance to be tested. The gradient chamber has an upper and a lower compartment which are separated from one another by the organ or tissue sample. One compartment of the gradient perfusion chamber is to be flushed with a nutrient solution while the organ or tissue sample is exposed to the substance to be tested, preferably via the other compartment.

The test results are evaluated using antibodies or antigens for the detection of whether certain cells in the tested organ or tissue sample are still present after the test (cultivation) or have died during treatment. Such detection can be accomplished by microscopic examinations, or other means.

Organ or tissue samples are not cell cultures of simple structure, but interactive tissue culture systems with the following advantages:

1. Interactive tissue culture systems are composed of cells in the organ-typical differentiation state. Depending on the tissue type, there is contact inhibition for some of the cells. These cells do not proliferate. They are embedded in a specific extracellular matrix and form structured cell associations with organ-typical function.

2. Interactive tissue culture systems consisting of cell associations which are composed of identical and different cells in an organ-specific matrix. Thus intercellular interactions can be acquired in the action of toxic substances between the different cell components.

3. Tests of toxic substances in interactive tissue culture systems can contribute to reduction of test numbers. There are two important advantages of the invention, specifically:

Substances which did not exhibit toxic effects in the cell culture system, since they become evident only by intercellular interactions, can be precluded early from other tests by using cell culture systems. The interactive cell culture model as claimed in the invention enables use of human tissue material. Thus the process, as described in the invention, is better suited than the existing processes for applying data acquired in the culture experiment to the situation in the human organism. This contributes to a reduction in the number of experiments.

The interactive tissue culture system as described in the invention also satisfies the following requirements:
  prevention of necrosis formation in the cultivated tissue
  abandonment of undefined medium additives
  preservation of an organ-specific degree of cell differentiation
  acquisition of organ-typical tissue composition
  possibility of specific basal or apical application of test substance.

Organ or tissue parts are obtained in the process, embodied by the invention without proteolytic preparation while acquiring the organ-typical tissue composition and while obtaining a organ-typical degree of cell differentiation. The tissue or organ samples can be obtained as tissue sections, for example, vibratome sections which can be obtained from all organs, as teased-out preparations, such as tissue explants from the kidneys, or mucosa explants of the stomach. Further, relatively thin tissue parts, for example, the retina, cornea, skin, etc., can also be used as tissue samples.

Only by using the gradient perfusion chamber is it possible to preserve the organ structure and the function which are linked to a functioning vascular system, such that disintegration of the tissue is prevented. In a normal culture dish with a nutrient solution, the process as described in the invention, cannot be carried out, since sufficient supply of nutrients, and especially oxygen, is not ensured. Only use of the unique gradient perfusion chamber prevents metabolites, which are naturally removed by the vascular system which supplies the organ, from accumulating in the tissue. Cultivation of a tissue sample in a conventional culture disk results in tissue necroses, destroying the original tissue structure. An assessment of whether this occurrence is the consequence of the action of toxic substance, or whether it is the consequence of culture conditions is no longer possible. These defects are avoided in the invention.

In the process embodying the invention, the location of the application can also be of decisive importance for the action of the substance to be tested. Epithelial cell associations are for example organized to be flat. The cells with the apical membrane border a lumen which can contain very different substances depending on the organ (for example, bladder—urine, intestine—digestive pulp, etc). The cell basal membrane conversely is in contact with the blood-like tissue fluid. Depending on the location of the application (basal or apical), test substances can have very different effects on the cells, at the same time substance gradients in tissue parts can greatly influence the intercellular interactions.

The invention focuses on the fact that toxic actions are triggered not only via direct contact of the test substance with a certain cell type, but are mainly conveyed via interactions between the different cells of an organ. In the process embodying the present invention these interactions are fully considered by the use of organ or tissue samples which represent an interactive tissue system.

Organs have a complex structure and they are composed of more than one cell type. The cells are present in different stages of differentiation. In addition to so-called reserve cells, which are necessary for replacement of dead tissue, terminally differentiated cells occur which no longer profile, but perform a specific function. With reference to the proliferation capacity of the differentiated cells, contact inhibition prevails. As long as the tissue association is undamaged, the specific extracellular matrix is intact and the cells are linked to one another, and they remain in their high differentiation state. Reserve cells are only activated to close wounds or for regeneration. The percentage of reserve cells capable of proliferation and the lifetime of the terminally differentiated cells are organ-specific. While the epithelial cells of the skin are replaced within a short time, for the epithelial cells of the kidneys have a lifetime of several years. If tissues are cultivated in the presence of mitogenic nutrient media, this acts to stimulate the reserve cells. Cell proliferation is excited, but not their differentiation. This changes the organ-typical ratio of proliferating to differentiated cells, and the typical organ function is limited. To approach organ-typical conditions as closely as possible in the tissue culture, as embodied in the invention, tissue material and a nutrient medium must be used which has with a cellular composition which corresponds to the ratios in the organ with reference to the degree of differentiation.

Organ function is determined both by its individual components and also by the interaction between the different cell types. Not only cells of the same type are in contact with one another, but also the cells of different tissue components interact with one another. In addition, not only the cellular components, but also the organ-typical extracellular matrix are of decisive importance for organ-typical interactions. Only by the interaction of the various tissue components does organ function become possible. This complexity, which can be of decisive importance for determination of the action of the substance, is not achieved by simple cell culture systems nor by co-culture systems.

Therefore, the invention takes into account the circumstance that in the organism a substance acts not only on a single cell type, but fundamentally on all cells of the body which come into contact with the substance or its metabolic products. For the toxicity of a substance therefore not only its acute action on an individual cell is decisive. Rather, there are intercellular interactions between the different cell types which, when influenced by the test substance, are responsible for its action in the organism.

In the process embodied in the invention, through the use of animal tissue or samples of human tissue test conditions can be established which enable direct applicability of the culture or test results to the conditions in an animal and human organism.

BRIEF DESCRIPTION OF THE DRAWING

The invention is detailed below in conjunction with the following figure:

FIG. 1 shows in simplified form a section through the gradient perfusion chamber.

DETAILED DESCRIPTION OF THE INVENTION

Perfusion chamber 1 shown in FIG. 1, includes two housing parts 2 and 3 which form a housing interior closed to the outside when the housing is in the closed position. Between two housing parts 2 and 3 there is a holder 4, formed by a retaining ring, on which the tissue or organ sample 5 is inserted and fixed. In this form globularization of an organ sample 5 is prevented. Holder 4, and organ or tissue sample 5, divide the interior of chamber 1 into two component spaces 6 and 7, each of which have an inlet 8 for supplying a nutrient solution or substance to be tested and an outlet 9, for removing the nutrient solution with the metabolic products, or the test substance. For example, the figure has the upper component space 6 is filled with the test substance. For this purpose, inlet 8 of this component space, is connected via a hose line 10 with a charge, not shown, for the test substance. The nutrient solution flows through lower component space 7. Inlet 8 there is connected via a hose line 11 and a multiple hose pump 12 with a reserve 13 for the nutrient solution. Outlet 9 of lower component space 7 is connected via a hose line, not shown, to a receiving tank for collecting used nutrient solution. In each test, it is preferred that several tissue samples 5 are cultivated at the same time and are partially exposed to the test substance.

Because a medium flows continuously especially through lower component space 7, metabolites and paracrine factors are continuously removed. Furthermore, optimum oxygen supply of respective tissue sample 5 is ensured. In a culture medium (nutrient solution) additives are abandoned which influence the test result, especially fetal sera (fetal calf serum), tissue extracts, etc. which are needed in nutrient solutions for cultures in culture dishes and which consist of a plurality of protein, growth factors, and other components which are not precisely defined and which adversely affect the test result, or which could lead to uncontrollable interference with the respective test substance. Use of perfusion culture techniques also minimize necroses.

Use of the perfusion chamber makes it easily possible to allow the respective test substance to act selectively basally or apically on tissue sample 5. Gaseous, liquid, or viscous substances are possible as the test substance.

As an example, the detection of the toxic action of vitreous body replacements in a renal explant culture is reproduced in the following for the process as embodied in the invention.

EXAMPLE

Vitreous body replacements, as the name indicates, are used for replacement of damaged or injured vitreous body in ophthalmology. In this example, two of these replacements (the substances perfluorophenathrene and perfluorodecaline) were studied. The substances have been tested in a cell culture system. This test yielded no indications of toxic effects of the vitreous body replacements. A test of the substance perfluorophenathrene in a rabbit eye however resulted in extensive changes of the blood vascular system in the area of the retina and major damage to the eye. The substance perfluorodecaline showed good tolerance in an animal test. No damage to the retina or other parts of the eye were observed.

An interactive tissue culture system was established for testing of toxicity. The culture system should provide information on whether the action of the substance perfluorophenathrene which changes the vessels can be established in vitro. Explants of neonatal rabbit kidneys were chosen as the test tissue. Antibodies for detection of vessels in the rabbit tissues are available in laboratory. In addition, the vascular system in this tissue has an extraordinarily high degree of spacial order. The preservation of the structure of the vascular system after application of the test substance was the parameter for assessment of the toxic effect in this test.

Material and methods:

Tissue preparation: One to three day old rabbits were sacrificed by cervical dislocation. Organ explants were prepared immediately after removal of the kidneys.

The kidneys of neonatal rabbits are not yet completely developed. In the outermost region of the organ directly under the organ capsule, all nephron developments stages are found in addition to the embryonal tissue. Microsurgical organ explants were prepared from this region. To do this the kidneys were cut in half lengthwise. With fine tweezers the thin organ capsule was removed. With the organ capsule, the renal tissue still in development was detached. Proteases were not used in this preparation method, i.e. the organ-typical extracellular matrix and the intercellular connections remained intact. The organ explants were then stretched onto the retaining ring system.

Culture of the kidney explants: By using a retaining ring system it was possible to use tissue explants which had been obtained by proteolytic disintegration for the tests. The tissue fragment was prepared in the corresponding size and fixed in the retaining ring. Proteolytic disintegration of the tissue, as can be necessary for culture in the conventional culture dish applications, was not carried out. The tissue fragment stretched onto the retaining ring was brought into contact with the tissue top or bottom with the test substance. The tissue top was defined as the side covered by the organ capsule. The tissue bottom was the tissue side exposed by the preparation. The tissue explants prepared in this way were cultivated with continuous throughflow of the medium. Use of perfusion culture technique in this case enabled complete abandonment of additives of fetal calf serum, adult serum or tissue extracts. The medium consists of a commercially available basic medium (Iscove's Modified Dulbecco's Medium, IMDM) to which the hormones aldosterone ($10^{-7}$M) and 1.25 dihydroxyvitamin $D_3$ ($10^{-9}$M) have been added. In the presence of these hormones the structure of the renal tissue is completely preserved. Necroses were not observed even after culture times of more than 10 days.

For the perfusion culture, stretched explant 5 (organ samples) were inserted into the gradient chamber so that one upper and one lower compartment 6 or 7 are formed which are separated from one another by tissue 5. Upper compartment 6 was filled with the given test substance and no flow takes place through it in the experiment since the test substance was of viscous consistency. Throughflow of the test substance however would be possible in the application of liquid or gaseous substances.

Lower compartment 7 was filled with nutrient solution which was continuously pumped through the chamber compartment. Storage bottle 13 of the medium was connected via a hose connection 11 to the inlet 8 of lower chamber 7. Chamber outflow 9 was connected to the waste bottle. Storage bottle 13 was kept at 4° C. during the entire culture time. Supply hose 11 was inserted into 12 which ensured constant flushing of chamber with medium at 1 ml/h. This perfusion rate was found to be very suitable for the culture of renal tissue. Fundamentally other flow rates are possible.

The test substance (substance perfluorophenathrene, substance perfluorodecaline) was added to the upper chamber compartment 6 so that the tissue fragment 5 was reached on one side by the nutrient solution, while opposite tissue side was in direct contact with the test substance. The control consisted in that upper chamber compartment 6 was not filled with test substance, but with basic medium.

Another experiment was designed such that in perfusion chamber 1, the test substance was placed in the lower chamber compartment 7, while the nutrient solution was pumped through the upper compartment 6. A number of perfusion chambers were placed on a heat plate with a temperature of 37° C. and the tissues were cultivated for 24 hours with continuous throughflow of medium.

After culture, the explants were flushed briefly in a buffer solution and frozen in liquid nitrogen.

Optical microscopic evaluation process: Two parameters were used as the criteria for assessment of the toxic effect of the respective test substance:

1. The different cell types of an organ are characterized by the expression of typical molecules which can be detected using specific antibodies. Endothelial cells in the rabbit kidneys likewise bear these molecules.

To detect endothelial cells, in our experiments antibody EC 1 was used. The EC 1 antigen is expressed solely by endothelial cells. If the endothelial cells die, the EC 1 antigen can no longer be detected in the tissue.

2. The developing vascular network of the kidneys is characterized by an extremely high degree of spacial order. This characteristic structure is observed only in a distinct differentiation state of the tissue. It is an expression of the coordinated development of different organ components of the kidneys. Preservation of the three-dimensional structure of the vascular network in the explant after application of the test substance was another criterion for assessment of the toxicity of the substance.

To detect endothelial antigens in the histological preparation, indirect immune peroxidase marking was used. In this process, murine monoclonal antibody EC 1 was used as a primary antibody for detection of endothelial cells. The antibody bonding was then detected in a second step by marked species-specific secondary antibodies.

The specificity of the antibody reaction was safeguarded by different controls. On the one hand control sections which have been treated not with the primary antibody but with all other fixing agents, buffers and antibody conjugates used were carried along. In addition, in the experiments sections with irrelevant primary antibodies of the same class or subclass of the specific antibody were incubated. Murine preimmune sera were used for control.

The results for application of the test substances in the lower chamber compartment are reproduced. Renal explants which had been cultivated with the substance perfluorophenathrene for 24 hours, like the control explants, showed optimum preservation of the spacial organization of the vascular network. In contrast, the vascular network which was exposed to the substance perfluorophenathrene for 24 hours was largely decomposed. Individual endothelial cells however were detectable, i.e. expression of the EC 1 antigen was not influenced by the incubation of the tissue with the substance perfluorophenathrene. The destructive action of substance perfluorophenathrene on the structural preservation of the vascular network was however unambiguous. In addition, the entire tissue structure showed structural changes. The results of the tests are summarized in the following table.

| Detection of the Toxic Effect of Vitreous Body Replacements in the Renal Explant Culture | | | |
|---|---|---|---|
| | Perfluorophenathrene | Perfluorodecaline | Control |
| Expression of EC 1 antigen | + | + | + |
| Vascular structure | – | + | + |
| Tissue structure | changed | + | + |

Legend: – antigen/structure no longer detectable, + antigen/structure clearly detectable The test of the vitreous body replacements perfluorophenathrene and perfluorodecaline on renal explants, in vitro, convincingly confirmed the results which were obtained after application of these substances to the rabbit eye. While perfluorodecaline did not cause damage to the retina or eye, the vascular system of the retina after application of perfluorophenathrene showed significant changes. Also the vascular system in the renal explants was already decomposed after 24 hours of incubation with perfluorophenathrene. Both the control explants and the explants incubated with perfluorodecaline after 24 hours of culture exhibited excellent preservation of the vascular system. This result clearly shows that interactive tissue culture systems can be successfully used for detection of toxic effects.

In the testing of the substance perfluorophenathrene on tumor cells there were no toxic effects of the substance. The importance of the cellular interaction for the shaping of the toxic effect of a substance is impressively highlighted by this discrepancy. Cell culture systems are outstandingly suited for detection of acute toxic effects. They allow prompt testing of the direct toxic effect. If the toxicity of a substance is however based on cellular interactions, other systems must be used for analysis.

The culture conditions described here by way of example can be varied as required. Variation of the flow rates of the medium, culture time intervals of varied length, and a different medium composition depending on the tissue requirement are possible and can be easily adapted. In addition to the teased-out preparations described here, tissue sections or organ parts can also be cultured.

Likewise other methods can be used for evaluation. In addition to techniques using transmission and raster electron microscopes, in-situ hybridization and biochemical and histochemical detection are conceivable. One important simplification of the evaluation can be achieved by measurement of molecules in the culture supernatant. For example, detection of the increase of apoptotic cells after application of test substances could be done via studying of the culture supernatant using apoptosis markers and suitable analysis systems.

For the tests described herein, explants of neonatal rabbit kidneys were used. Fundamentally any tissue can be cultivated with this system. In our laboratory, initial experiments with tissues from the rabbit stomach showed that this tissue can also be cultivated with good success over long time intervals. The use of a gradient perfusion chamber described herein, for specific apical or basal application of toxic substances, is also possible for other tissues (for example, stomach, skin, cornea, retina).

For the experiments described herein, a culture duration of 24 hours was chosen. Shorter or longer culture intervals are possible with this system.

It was assumed above that the tissue sample is frozen prior to evaluation to improve storage. It is also possible to immediately evaluate the tissue sample after its cultivation.

For the evaluation process other techniques are also possible, for example, automated test systems, for example, the test system known to one skilled in the art under ELISA. Instead of the aforementioned EC 1 antigen, other markers can also be used for evaluation, for detection of proliferating and/or apoptotic cells.

Reference Number List
1 perfusion chamber
2,3 housing part
4 holder
5 tissue or organ sample
6,7 component space
8 inlet
9 outlet
10,11 hose line
12 hose pump
13,14 reserve tank

What is claimed is:

1. A process for determining the tolerance or toxicity of gaseous, liquid and/or viscous substances for a human or animal organism comprising the steps of placing a tissue sample which has been obtained without proteolytic disintegration, in a gradient perfusion chamber which comprises, in an interior of said chamber, at least two component spaces which are separated from one another by said tissue sample; supplying a nutrient solution to said tissue sample wherein said tissue sample which is exposed to a test substance via at least one of said at least two compartments, thereby effectuating cultivation of said tissue sample and evaluating said tissue sample for the tolerance or toxicity of the test substance.

2. The process as claimed in claim 1, wherein said tissue sample is supplied with said nutrient solution via a first chamber defining a first component space in said perfusion chamber and is exposed to said test substance via a second chamber defining a second component space, in such perfusion chamber.

3. The process as claimed in claim 1, wherein said tissue sample is a tissue section or a teased-out preparation from a living animal or human tissue.

4. The process as claimed in claim 1, wherein said tissue sample is a thin tissue part, selected from the group consisting of a retina tissue sample, a cornea tissue sample, and a skin tissue sample.

5. The process as claimed in claim 1, wherein the step of evaluating said tissue sample after cultivation is by the use of antigens which are expressed solely by an organ-typical, differentiated cell type.

6. The process as claimed in claim 1, wherein the step of evaluating said tissue sample, after cultivation is by a microscopic evaluation.

7. The process as claimed in claim 6, wherein said microscopic evaluation is an optical microscopic evaluation.

8. The process as claimed in claim 1, further comprising the steps of flushing said tissue sample, after cultivation, in a buffer solution and then flash freezing said tissue sample, in liquid nitrogen.

9. The process as claimed in claim 1, wherein the step of evaluating said tissue sample, after cultivation, is by the use of markers for detection of proliferating and/or apoptotic cells.

10. The process as claimed in claim 1, wherein the step of evaluating said tissue sample, after cultivation, is by the use of an EC1 antigen which is expressed solely by endothelial cells.

* * * * *